United States Patent
Wood et al.

(10) Patent No.: US 8,523,956 B2
(45) Date of Patent: Sep. 3, 2013

(54) COLOURING COMPOSITION FOR KERATIN FIBRES

(75) Inventors: Jonathan Wood, Weinheim (DE); Dominic Pratt, Büttelborn (DE); Anja Aechtner, Mannheim (DE); Kristin Olsson, Ladenburg (DE); Takeshi Iizaki, Tokyo (JP)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/583,745

(22) PCT Filed: Sep. 7, 2010

(86) PCT No.: PCT/EP2010/005487
§ 371 (c)(1),
(2), (4) Date: Sep. 10, 2012

(87) PCT Pub. No.: WO2011/113452
PCT Pub. Date: Sep. 22, 2011

(65) Prior Publication Data
US 2013/0000056 A1    Jan. 3, 2013

(30) Foreign Application Priority Data
Mar. 15, 2010  (EP) ..................................... 10002686

(51) Int. Cl.
*A61Q 5/10* (2006.01)
(52) U.S. Cl.
USPC ................ 8/405; 8/406; 8/408; 8/410; 8/421; 8/455
(58) Field of Classification Search
USPC ...................... 8/405, 406, 408, 410, 421, 455
See application file for complete search history.

(56) References Cited

U.S. PATENT DOCUMENTS

| | | | |
|---|---|---|---|
| 4,314,809 A | 2/1982 | Rose et al. | |
| 2002/0166180 A1 | 11/2002 | Chassott et al. | |
| 2005/0081311 A1* | 4/2005 | Schmenger et al. | 8/405 |

FOREIGN PATENT DOCUMENTS

| | | |
|---|---|---|
| CA | 2 613 049 A1 | 4/2008 |
| WO | 2004/019895 A1 | 3/2004 |
| WO | 2005/123019 A1 | 12/2005 |

OTHER PUBLICATIONS

International Search Report Dated Dec. 14, 2010, Mailed Jan. 4, 2011.

* cited by examiner

*Primary Examiner* — Eisa Elhilo
(74) *Attorney, Agent, or Firm* — Norris McLaughlin & Marcus P.A.

(57) ABSTRACT

Present invention relates to a coloring composition for keratin fibers especially for human hair with exceptionally improved color and shade stability. Accordingly, the first object of the present invention is a coloring composition for keratin fibres especially human hair comprising, in a cosmetically acceptable medium, at least one oxidative dyestuff precursor, 1,3-bis(2,4-diaminophenoxy) propane and/or its respective salts as a coupling agent and at least one direct dye. In an especially preferred from of the present invention the coloring compositions are substantially free from mono cyclic m-phenylenediamine coupling agent. With the term "mono cyclic m-phenylenediamine", it is meant that the compound comprises only one cyclic group, preferably a benzene ring, in its molecule.

14 Claims, No Drawings

COLOURING COMPOSITION FOR KERATIN FIBRES

Present invention relates to a colouring composition for keratin fibres, especially for human hair, with exceptionally improved colour and shade stability.

Oxidative colouring for keratin fibres has been commonly used for ages in hair dressing practice. Colours achieved with oxidative dyestuffs are usually long lasting and have high level of gray coverage. Despite these advantageous properties, colour directions are often observed to change even in a relatively short period after colouring hair. This problem is even aggravated when hair is previously multiple processed with either oxidative or reducing treatments so that various hair parts have different level of damage. In these cases, colour direction differences are observed between the parts closer to the scalp, the part with lower level of damage, and towards to ends, the parts with higher level of damage, resulting in an inhomogeneous colour appearance.

In oxidative colouration, brown colours are achieved with the use of so called blue coupling agents such as m-phenylenediamines. It has been found out that the colour direction changes take place in a relatively short period of time after colouring hair when monocyclic m-phenylenediamines are used as coupling agents.

Additionally, direct dyes are often used for shading or fine tuning the shades, colour direction. Due to relatively weaker resistance against washing and/or any other environmental influences compared to the oxidative dyes, colour direction changes becomes visible in a relatively short period of time after colouration which disturb the cosmetic appearance of hair.

In order to overcome and/or improve the colour and especially colour shade stability of oxidative colours, the inventors of the present invention have surprisingly found out that an oxidative colouring composition comprising at least one di cyclic m-phenylenediamine and at least one direct dye in addition to an oxidative dyestuff precursor, wherein the composition is free of any mono cyclic m-phenylenediamine, shows excellent stability against washing and any other environmental influences and therefore delivers long lasting colours and especially without or with minimum changes in colour direction, shade. This effect is especially excellent with brown colours and in particular with any of so called cool brown shades.

Accordingly, the first object of the present invention is a colouring composition for keratin fibres especially human hair comprising, in a cosmetically acceptable medium, at least one oxidative dyestuff precursor, 1,3-bis(2,4-diaminophenoxy) propane and/or its respective salts as a coupling agent and at least one direct dye.

Further object of the present invention is the use of a composition comprising, in a cosmetically acceptable medium, at least one oxidative dyestuff precursor, 1,3-bis(2,4-diaminophenoxy) propane and/or its respective salts as a coupling agent and at least one direct dye for oxidative colouring keratin fibres, especially human hair.

Still further object of the present invention is the use of a composition for colouring keratin fibres especially human hair comprising, in a cosmetically acceptable medium, at least one oxidative dyestuff precursor, 1,3-bis(2,4-diaminophenoxy) propane and/or its respective salts as a coupling agent and at least one direct dye for achieving long lasting shades, preferably brown, blond, red and violet shades.

In an especially preferred form of the present invention the colouring compositions are substantially free from mono cyclic m-phenylenediamine coupling agent.

With the term "mono cyclic m-phenylenediamine", it is meant that the compound comprises only one cyclic group, preferably a benzene ring, in its molecule.

Composition of the present invention comprises at least one oxidative dye precursor. Some examples are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylenediamine, 2-(2,5-diaminophenyl)ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and 1,2,4-triamino benzene, or the water-soluble salts thereof.

Preferably, at least one oxidative dyestuff precursor is selected from p-phenylenediamines, and substituted p-phenylenediamines such as 2,5-diamino-toluene, 2-(2,5-diaminophenyl)ethanol, 1-amino-4-bis-(2'-hydroxy-ethyl)amino-benzene, p-aminophenols such as p-methylaminophenol, pyrazols such as 1-hydroxyethyl-4,5-diaminopyrazole, pyrimidines such as tetramino pyrimidines, triaminohydroxy pyrimidines, and indols and indolines such as 6-hydroxyindole, 5,6-dihydroxyindole, 5,6-dihydroxyindoline and their respective salts.

More preferably at least one oxidative dye precursor is selected from p-phenylenediamine, 2,5-diamino-toluene, 2-(2,5-diaminophenyl)ethanol, 1-amino-4-bis-(2'-hydroxyethyl)amino-benzene, p-aminophenol, p-methylaminophenol, 1-hydroxyethyl-4,5-diaminopyrazole and their respective salts.

Total concentration of oxidative dye precursors are in the range of 0.01 to 10% by weight, preferably 0.05 to 7.5% by weight and more preferably 0.1 to 5% by weight, calculated to total composition prior to mixing with an oxidizing agent.

Total concentration of 1,3-bis(2,4-diaminophenoxy) propane and/or its respective salts is in the range of 0.001 to 5% by weight, preferably 0.005 to 3% by weight and more preferably 0.01 to 2.5% by weight, calculated to total composition prior to mixing with an oxidizing agent.

The composition according to the invention preferably comprises one or more additional coupling substance. Suitable ones are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2- methylamino-6-methoxypyridine, 2-amino-3-hydroxypyridine, 2-dimethyl-amino-5-aminopyridine, 2,6-diaminopyridine, 5-amino-2-methylphenol, 2-methyl-5-hydroxyethylaminophenol, 2-methyl-5-amino-6-chlorphenol, 2-bis(2-hydroxyethyl)aminotoluene, 2-amino-5-methylphenol, α-naphthol, 4,6-dichlororesorcinol, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxybenzene, 5-amino-2-methoxyphenol, hydroxybenzomorpholine, 1,2,4-trihydroxybenzene, phenylmethylpyrazolone, 3-amino-2,4-dichlorophenol, hydroxyethyl-3,4-methylenedioxyaniline, 2,6-dimethoxy-3,5-dimethylpyridine, 5-amino-4-chloro-2-methylphenol, hydroxypropyl-bis-(N-hydroxyethyl-p-phenylenediamine), 1-acetoxy-2-methylnaphthalene, 2,2'-methylenebis-4-aminophenol and/or or their respective salts.

Preferably one or more couplers are selected from resorcinol, 2-methyl resorcinol, 4-chlororesorcinol, 3-amino-phenol, 1-methyl-2-hydroxy-4-aminobenzene, 2,6-dihydroxy-3,4-dimethylpyridine, 4-amino-3-methylphenol, 6-amino-3-methylphenol, 3-amino-2-methylamino-6-methoxypyridine, 2-amino-3-hydroxy-pyridine, 2-methyl-5-hydroxyethylaminophenol, 2-methyl-5-amino-6-chlorphenol, α-naphthol, 1,5-dihydroxy naphthalene, 2,7-dihydroxy naphthalene, 1-hydroxy-2-methyl naphthalene, hydroxybenzomorpholine, 1,2,4-trihydroxybenzene, phenylmethylpyrazolone, 3-amino-2,4-dichlorophenol, hydroxyethyl-3,4-methylenedioxyaniline, 2,6-dimethoxy-3,5-dimethylpyridine, 5-Amino-4-chloro-2-methylphenol, hydroxypropyl-bis-(N-hydroxyethyl-p-phenylenediamine), 1-acetoxy-2-methylnaphthalene, 2,2'-methylenebis-4-aminophenol and/or or their respective salts.

More preferably, one or more additional couplers are selected from resorcinols such as resorcinol, 2-methyl resorcinol, 4-chlororesorcinol and/or m-aminophenols such as 3-amino-phenol, 1-methyl-2-hydroxy-4-aminobenzene, 2-methyl-5-hydroxyethylaminophenol, 2-methyl-5-amino-6-chlorphenol and/or their respective salts.

Total concentration of one or more coupling substances and their salts is in the range of 0.01 to 5% by weight, preferably 0.05 to 3% by weight and more preferably 0.1 to 2.5% by weight, calculated to total composition prior to mixing with an oxidizing agent.

Composition of the present invention comprises one or more direct dyes. Direct dyes are found to be useful for adjusting colour tone within the meaning of the present invention.

Direct dyes suitable are cationic, anionic and/or nitro dyes. Suitable non-limiting examples to cationic ones are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Suitable non-limiting examples to anionic ones are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Suitable non-limiting examples to nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

In an especially preferred form of the present invention, at least one direct dye is selected from direct dyes having a $\lambda_{max}$ in the range of 400 to 460 nm, preferably 410 to 450 nm and more preferably 415 to 445 nm measured in ethanol-water mixture 50/50, by weight.

Preferred direct dyes are cationic dyes such as Basic Orange 31, Basic Yellow 57 and Basic Yellow 87, anionic dyes such as Acid Yellow 1, Acid Yellow 23, Acid Yellow 3, D&C Orange No. 4, and Disperse Black 9 and nitro dyes such as HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

More preferred direct dyes are cationic dyes such as Basic Orange 31, Basic Yellow 57 and Basic Yellow 87 and nitro dyes such as HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

Most preferred are nitro dyes and especially those of HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

Total concentration of one or more direct dyes is in the range of 0.001 to 2.5% by weight calculated to total composition prior to mixing with oxidizing agent.

pH of the composition is in the range of 5 to 12, preferably 6 to 11 and more preferably 6.8 to 10, after mixing with an oxidizing agent.

Composition of the present invention is mixed prior to application onto hair with a composition comprising at least one oxidizing agent. The preferred oxidizing agent is hydrogen peroxide at a concentration of 0.5 to 12% by weight. Other peroxides such as urea peroxide and melanin peroxide are also possible to use.

At the same time the subject of the present invention is process for colouring keratin fibres especially human hair wherein a composition comprising in a cosmetically acceptable medium, at least one oxidative dyestuff precursor, at least one di cyclic m-phenylenediamine as a coupling agent and at least one direct dye, is mixed with an oxidizing composition comprising at least one oxidizing agent and applied onto hair and processed for 10 to 45 min at a temperature of 20 to 45° C. and rinsed off from hair.

The mixing ratio of the composition comprising in a cosmetically acceptable medium, at least one oxidative dyestuff precursor, at least one di cyclic m-phenylenediamine as a coupling agent and at least one direct dye and oxidizing composition comprising at least one oxidizing agent is preferably in the range of 3:1 to 1:3, by weight, more preferably in the range of 2:1 to 1:2, by weight, and in particular 1:1, by weight.

Composition of the present invention can comprise additionally substances customarily found in colouring compositions.

Compositions of the present invention can be in the form of solutions, dispersions, gels and emulsions. Most preferred is emulsion.

Colouring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition, prior to mixing with oxidizing agent. Non-limiting examples are myristic acid, palmitic acid, behenic acid, stearaic acid, oleic acid, linoleic acid. The most preferred fatty acid is oleic acid.

Colouring composition of the present invention comprise at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol content should be in the range of 1 to 20% by weight, calculated to total composition prior to mixing with an oxidizing agent.

Colouring compositions according to present invention comprises surfactants selected from anionic, amphoteric (or zwiterionic) and/or cationic surfactants as emulsifier or solubilizer. Cationic surfactants are as well used as hair conditioners in the colouring composition.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth-20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula

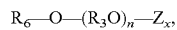
$$R_6-O-(R_3O)_n-Z_x,$$

wherein $R_6$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$— alkyl dimethyl amineoxides such as lauryl dimethyl aminoxide, $C_{12}$-$C_{18}$— alkyl amidopropyl or -ethyl amineoxides, $C_{12}$-$C_{18}$— alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Anionic surfactants suitable within the scope of the invention are in principal known from the cleansing compositions and may be present in an amount from 0.1 to about 10% by weight, calculated to the total composition prior to mixing with an oxidizing agent. Compatibility of anionic surfactant in the composition should be taken into account when choosing the type and the concentration.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

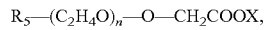
$$R_5-(C_2H_4O)_n-O-CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

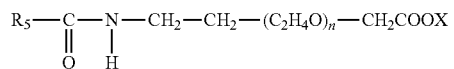
$$R_5-\underset{\underset{O}{\|}}{C}-\underset{\underset{H}{|}}{N}-CH_2-CH_2-(C_2H_4O)_n-CH_2COOX$$

wherein $R_5$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants in a mixture.

An overview of the anionic surfactants suitable for the present invention can furthermore be found in the monography of K. Schrader, "Grundlagen and Rezepturen der Kosmetika", $2^{nd}$ Ed. (1989, Hüthig Buchverlag), pp. 595-600 and pp. 683 to 691.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Colouring composition can comprise cationic surfactants as emulsifier, solubilizer and/or conditioning ingredients according to the formula,

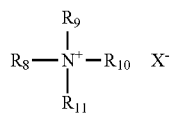

where $R_8$ is a saturated or unsaturated, branched or non-branched alkyl chain with 8-22 C atoms or $R_{12}CONH(CH_2)_n$ where $R_{12}$ is saturated or unsaturated, branched or non-branched alkyl chain with 7-21 C atoms and n has typical value of 1-4 or $R_{13}COO(CH_2)_n$ where $R_{13}$ is saturated or unsaturated, branched or non-branched alkyl chain with 7-21 C atoms and n has typical value of 1-4, and $R_9$ is H or unsaturated or saturated, branched or non-branched alkyl chain with 1-22 C atoms or $R_{12}CO\,NH(CH_2)_n$ or $R_{13}COO(CH_2)_n$ where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Form the above mentioned surfactants preferred are non-ionic and anionic surfactants and their mixtures.

Total surfactant concentration is in the range of 0.5 to 15%, preferably 1 to 10%, more preferably 1 to 7.5% by weight calculated to total composition prior to mixing with an oxidizing agent.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46. Among those the most preferred one is the Polyquaternium 11 as well known with its trade name Gafquat from ISP and as Luviquat PQ from BASF.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

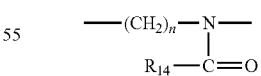

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

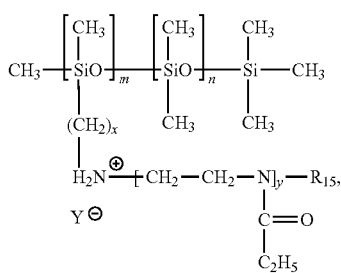

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Colouring compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methyl pyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total composition, prior to mixing with oxidizing composition.

Colouring compositions according to the invention may comprise thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition prior to mixing with oxidizing composition and depending on the desired consistency thereof.

Optionally, the colouring composition of this invention can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin and polyethyleneglycol mono or di fatty acid esters.

Compositions may further comprise at least one ubiquinone of the formula

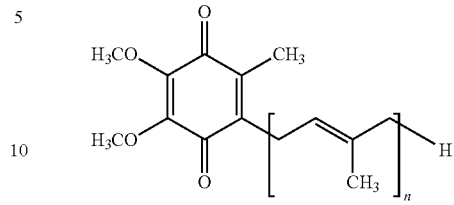

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition, prior to mixing with oxidizing composition.

The composition comprises ubiquinone which is preferably selected from the ones where n is a number between 6 and 10 and more preferably it is ubichinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition, prior to mixing with oxidizing composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition can comprise further ceramide type of compound with the general formula

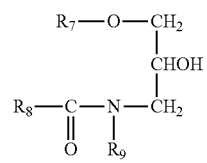

where $R_7$ and $R_8$ are independent from each other alkyl- or alkenyl group with 10 to 22 carbon atoms, $R_9$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Composition can comprise at least one diamine compound. Preferred diamide compounds are according to the general structure

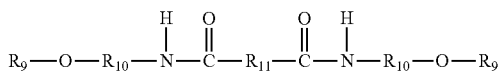

wherein $R_9$ is a linear or branched, saturated or unsaturated alkyl chain with 1 to 12 C atoms which may be substituted with hydroxy and/or alkoxy groups, preferably $R_9$ is linear or branched, saturated or unsaturated alkyl chain with 1 to 12 C atoms which may be substituted by 1 to 3 substituents selected from a hydroxy group and C1 to C6 alkoxy group, more preferably $R_9$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{10}$ is linear or branched alkyl chain with 1 to 5 C atoms, preferably linear or branched alkyl chain with 2 to 5 C atoms and more preferably an alkyl chain with 2 to 3 C atoms, and $R_{11}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

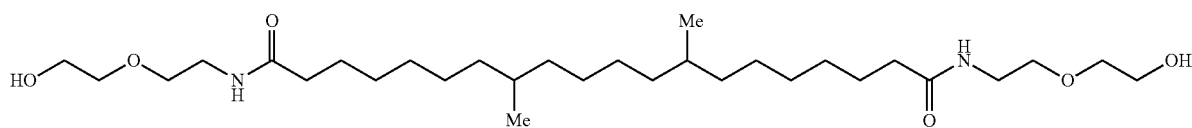

(A)

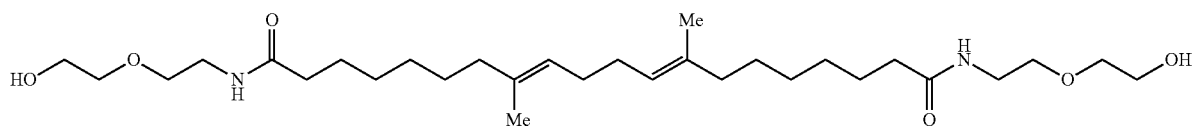

(B)

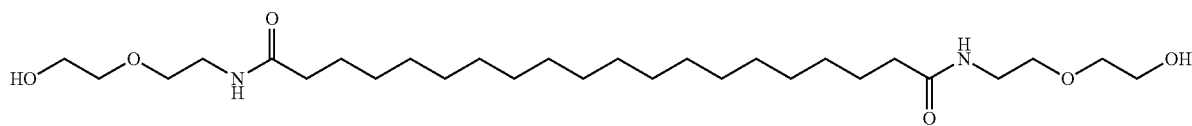

(C)

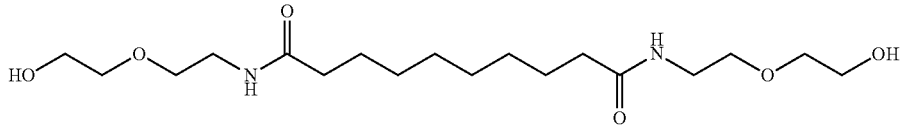

(D)

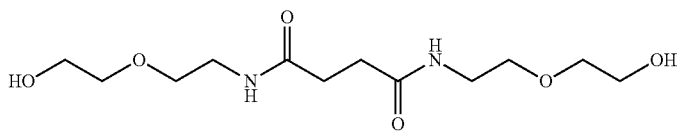

(E)

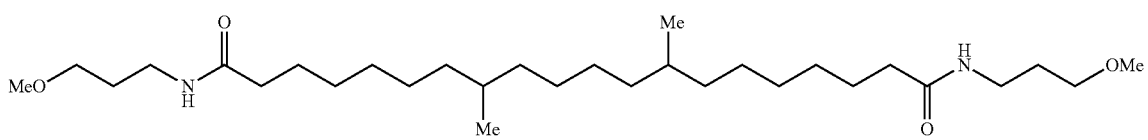

(F)

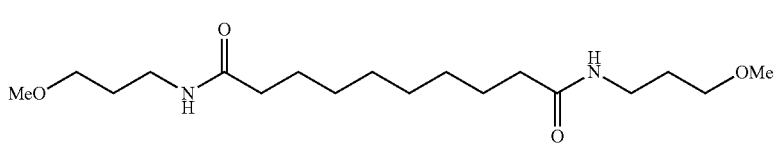

(G)

Particularly preferred diamide compound is the compound F which is bis (methoxypropylamido) isodocosane and commercially available from Kao Corporation—Japan.

Concentration of diamide compound is in the range of 0.001 to 5%, preferably 0.002 to 3% more preferably 0.005 to 2% and most preferably 0.01 to 1% by weight calculated to total composition, prior to mixing with oxidizing composition.

Additionally, one or more natural oil may be incorporated into the compositions of the present invention. Suitable are such as olive oil, almond oil, avocado oil, wheatgerm oil, ricinus oil or their mixture. Concentration of natural oil should be 0.01 to 2.5%, preferably 0.01 to 1%, more preferably 0.05 to 0.5% by weight, calculated to total each composition, prior to mixing with oxidizing composition.

Furthermore, composition of the present invention is suitably provided to the users in the form of a kit. Accordingly, further object of the present invention is a kit comprising a colouring composition for keratin fibres especially human hair comprising, in a cosmetically acceptable medium, at least one oxidative dyestuff precursor, at least one di cyclic m-phenylenediamine as a coupling agent and at least one direct dye, wherein preferably the composition does not comprise any mono cyclic m-phenylenediamine coupling agent, and a second composition comprising at least one oxidizing agent.

Compositions of the present invention can further comprise ingredients customarily found in such compositions such as alkalizing agents, preservatives antioxidants, fragrances, reducing agents and chelating agents.

The following example is to illustrate the present invention, but not to limit.

EXAMPLE 1

| Base composition | % by weight |
| --- | --- |
| Octyldodecanol | 1.3 |
| Cetearyl alcohol | 1.0 |
| Oleyl alcohol | 2.6 |
| Sodium lauryl sulphate | 1.0 |
| Xanthan gum | 1.0 |
| Sodium sulfit | 0.5 |
| Ascorbic acid | 0.2 |
| Tetrasodium EDTA | 0.2 |
| Fragrance, preservative | q.s. |
| Ammonia 25% | 8.0 |
| Water | q.s. to 100 |

| Dyestuff composition | Concentration (mMol/kg) | | | |
| --- | --- | --- | --- | --- |
| | A | B | C | D |
| p-toluenediamine sulphate | 26.8 | 26.8 | 26.8 | 26.8 |
| Resorcinol | 15.4 | 15.4 | 15.4 | 15.4 |
| m-aminophenol | 9.2 | 9.2 | 9.2 | 9.2 |
| 4-amino-2-hydroxytoluene | 1.5 | 1.5 | 1.5 | 1.5 |
| 2-amino-4-hydroxyethylaminoanisol | 1.2 | 0.6 | — | — |
| 1,3-bis(2,4-diaminophenoxy)propane HCl | — | 0.6 | — | 0.6 |
| HC Yellow 2 | — | — | 1.2 | 0.6 |
| ΔE Value | 12.16 | 10.6 | 12.56 | 9.43 |

Compositions A to D were prepared and hair streaks were coloured after mixing with a composition comprising hydrogen peroxide at a concentration of 6% by weight at a weight ratio of 1:1 which was resulted in a pH value of 9.5. After processing of 30 min at 40° C., the hair streaks were rinsed off with tap water and shampooed once with a commercial shampoo and dried with a hair drier. A homogeneously coloured hair streak into a cool brown colour was obtained. Colour and shade stability was tested by placing the coloured streaks into a surfactant solution comprising sodium laureth sulphate, an anionic surfactant, at a concentration of 4% by weight, and shaking for 30 min at approximately 30° C. at a speed of 100 rpm and measuring the L, a and b values before and after the test and calculating the ΔE values with the well known equation.

The calculated ΔE results are presented in the above table below each colouring composition. The lower the value is the lower the colour difference. It is clear from the above results; the lowest value was obtained with the composition D which is according to the present invention. It is also clear from the above results the stabilizing effect achieved with the two dyestuffs, 1,3-bis(2,4-diaminophenoxy)propane HCl and HC Yellow 2 is synergistic, i.e. the stabilizing effect of the two dyes (9.43−12.16=−2.73) is larger than the sum of the individual effects ((10.6−12.16=−1.56)+((12.56−12.16=0.40/2) =0.20)=−1.36). In other words, stabilizing effect of the individual dyes is less than the stabilizing effect of the combination of dyes 1,3-bis(2,4-diaminophenoxy)propane HCl and HC Yellow 2.

EXAMPLE 2

In order to show improved shade stability, number of competitors' products and compositions according to the present invention were tested for their wash fastness with the test method described under Example 1. It should be noted that all of the compositions produce a colour tone at the level of 6 and all of them are described to produce brown shade and more specifically a cool brown shade. Furthermore, inventive compositions were produced using the base composition disclosed under Example 1. The qualitative dyestuff compositions and a and b values before and after the test are given in the Table below.

|  | Competitor's product no | | | | Inventive composition no | | |
| --- | --- | --- | --- | --- | --- | --- | --- |
|  | 1 | 2 | 3 | 4 | 1 | 2 | 3 |
| p-Toluenediamine | X |  | X | X | X | X | X |
| p-Phenylenediamine |  | X |  |  |  |  |  |
| Resorcinol | X | X | X | X | X | X | X |
| 2,4-diaminophenoxyethanol HCl | X |  |  | X |  |  |  |
| 2-amino-4-hydroxyethylaminoanisole sulphate |  | X | X |  |  |  |  |
| m-Aminophenol | X |  | X | X | X | X | X |
| N,N-bis(2-hydroxyethyl)-p-phenylenediamine sulphate | X |  |  |  |  |  |  |
| 1-Naphtol |  |  |  |  |  |  |  |
| p-Aminophenol |  |  |  |  |  |  |  |
| 2-Methylresorcin |  |  |  |  | X |  |  |
| 1,3-bis(2,4-diaminophenoxy) propane HCl |  |  |  |  | X | X | X |
| 4-amino-2-hydroxytoluene |  |  |  |  |  |  | X |
| HC Yellow 2 |  |  |  |  | X | X | X |
| 2-Amino-3-hydroxypyridine |  |  |  |  |  | X |  |
| a value before | 0.17 | 1.12 | 1.92 | 2.47 | 2.47 | 1.02 | 1.83 |
| b value before | 1.23 | 1.34 | 5.97 | 5.97 | 0.74 | 1.20 | 2.62 |
| a value after | 3.07 | 3.63 | 4.42 | 4.77 | 3.66 | 3.07 | 3.65 |
| b value after | 10.50 | 11.30 | 11.19 | 12.90 | 4.07 | 3.16 | 4.07 |

From the above results, it is beyond any doubt that a and b values for colours obtained with inventive compositions changed much less than the values obtained with competitors' products.

The invention claimed is:

1. Colouring composition for keratin fibres especially human hair comprising, in a cosmetically acceptable medium, at least one oxidative dyestuff precursor, 1,3-bis(2, 4-diaminophenoxy) propane and/or its respective salts as a coupling agent and at least one direct dye, wherein said the composition is substantially free from mono cyclic m-phenylenediamines.

2. A Composition according to claim 1, wherein the at least one oxidative dyestuff precursor is selected from p-phenylenediamines, p-aminophenols, pyrazols, pyrimidines, indols and indolines and/or their respective salts.

3. A composition according to claim 1, wherein the at least one oxidative dye precursor is selected from p-phenylenediamine, 2,5-diamino-toluene, 2-(2,5-diaminophenyl) ethanol, 1-amino-4-bis-(2'-hydroxy-ethyl)amino- benzene, p-aminophenol, p-methylaminophenol, 1-hydroxyethyl-4,5-diaminopyrazole and their respective salts.

4. A composition according to claim 1, wherein the at least one direct dye is selected from anionic, cationic and nitro dyes.

5. A composition according to claim 1, wherein the at least one direct dye is selected from dyes having a $\lambda_{max}$ between 400 and 460 nm measured in ethanol-water mixture 50/50, by weight.

6. A composition according to claim 1, wherein the at least one direct dye is selected from Basic Orange 31, Basic Yellow 57 and Basic Yellow 87, anionic dyes such as Acid Yellow 1, Acid Yellow 23, Acid Yellow 3, D&C Orange No. 4, and Disperse Black 9 and nitro dyes such HC Orange No.1, HC Orange No.2, Yellow No.2, HC Yellow No.4, HC Yellow No.7, HC Yellow No.9, HC Yellow No.10, HC Yellow No.13, picramic acid, 3-nitro-4n-aminophenol, 2-hydroxyethylpicramic acid, 3-methylamino-4-nitrophenoxyethanol, 2-nitro-5-glycerylmethylaniline, 4-nitrophenyl aminoethylurea, hydroxy-2-nitro-p-toluidine, and 2-chloro-6-ethylamino-4-nitrophenol, and their respective salts.

7. A composition according to claim 1, wherein the at least one direct dye is selected from HC Orange No.1, HC Orange No.2, Yellow No.2, HC Yellow No.4, HC Yellow No.7, HC Yellow No.9, HC Yellow No.10, HC Yellow No.13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

8. A composition according to claim 1, comprising additionally one or more coupling substances, selected from 2-methyl resorcinol, 4-chlororesorcinol, 3-amino-phenol, 1-methyl-2-hydroxy-4-aminobenzene, 2.6-dihydroxy-3,4-dimethylpyridine, 4-amino-3-methylphenol, 6-amino-3-methylphenol, 3-amino-2-methylamino-6-methoxypyridine, 2-amino-3-hydroxyl-pyridine, 2-methyl-5-hydroxyethylaminophenol, 2-methyl-5-amino-6-chlorphenol, α-naphthol, 1, 5-dihydroxy naphthalene, 2,7-dihydroxy naphthalene, 1-hydroxy-2-methyl naphthalene, hydroxybenzomorpholine, 1,2,4-trihydroxybenzene, phenylmethylpyrazolone, 3-amino-2,4-dichlorophenol, hydroxyethyl-3,4-methylenedioxyaniline, 2.6-dimethoxy-3,5-dimethylpyridine, 5-Amino-4-chloro-2-methylphenol, hydroxypropyl-bis-(N -hydroxyethyl-p-phenylenediamine), 1-acetoxy-2-methylnaphthalene, 2,2'-methylenebis-4-aminophenol and or their respective salts.

9. A composition according claim 7, wherein the one or more additional couplers are selected from resorcinols of the group consisting of resorcinol, 2-methyl resorcinol, 4-chlororesorcinol and/or m-aminophenols of the group consisting of 3-amino-phenol, 1-methyl-2-hydroxy-4-aminobenzene, 2-methyl-5-hydroxyethylaminophenol, 2-methyl-5-amino-6-chlorphenol and/or their respective salts.

10. A composition according to claim 1, further comprising at least one alkalizing agent.

11. A composition according to claim 1, further comprising at least one fatty alcohol and/or at least one surfactant.

12. A composition according to claim 1, further comprising at least one oxidizing agent, hydrogen peroxide.

13. A process for colouring keratin fibres, especially human hair, wherein a composition according to claim 1 is mixed with a composition comprising at least one oxidizing agent and applied onto hair and after processing of 1 to 45 min at a temperature of 20 to 45° C. rinsed off from hair.

14. A kit comprising at least one composition according to claim 1 and a second composition comprising at least one oxidizing agent.

* * * * *